(12) United States Patent
Farsiu

(10) Patent No.: US 11,399,930 B2
(45) Date of Patent: Aug. 2, 2022

(54) SYSTEMS AND METHODS FOR PSYCHO-SIGNAL PROCESSING

(71) Applicant: Duke University, Durham, NC (US)

(72) Inventor: Sina Farsiu, Durham, NC (US)

(73) Assignee: Duke University, Durham, NC (US)

( * ) Notice: Subject to any disclaimer, the term of this patent is extended or adjusted under 35 U.S.C. 154(b) by 630 days.

(21) Appl. No.: 16/476,272

(22) PCT Filed: Jan. 23, 2018

(86) PCT No.: PCT/US2018/014756
§ 371 (c)(1),
(2) Date: Jul. 6, 2019

(87) PCT Pub. No.: WO2018/136907
PCT Pub. Date: Jul. 26, 2018

(65) Prior Publication Data
US 2019/0350698 A1    Nov. 21, 2019

Related U.S. Application Data

(60) Provisional application No. 62/449,192, filed on Jan. 23, 2017.

(51) Int. Cl.
| | | |
|---|---|---|
| A61F 2/14 | (2006.01) | |
| G06T 7/12 | (2017.01) | |
| G06T 7/13 | (2017.01) | |
| A61B 3/032 | (2006.01) | |
| A61B 3/14 | (2006.01) | |
| G06T 3/20 | (2006.01) | |
| G06T 3/40 | (2006.01) | |

(Continued)

(52) U.S. Cl.
CPC ............. *A61F 2/141* (2013.01); *A61B 3/032* (2013.01); *A61B 3/145* (2013.01); *G06T 3/20* (2013.01); *G06T 3/40* (2013.01); *G06T 5/002* (2013.01); *G06T 7/12* (2017.01); *G06T 7/13* (2017.01); *A61F 2/482* (2021.08); *A61F 2250/0002* (2013.01); *G06T 2207/10016* (2013.01); *G06T 2207/30041* (2013.01)

(58) Field of Classification Search
None
See application file for complete search history.

(56) References Cited

U.S. PATENT DOCUMENTS

| | | |
|---|---|---|
| 2001/0055340 A1 | 12/2001 | Kim et al. |
| 2008/0228242 A1* | 9/2008 | Fink .......................... A61F 9/08 607/54 |
| 2011/0037894 A1 | 2/2011 | Sbaiz |

(Continued)

OTHER PUBLICATIONS

International Search Report and Written Opinion for PCT/US18/14756 dated Apr. 5, 2018.

(Continued)

*Primary Examiner* — Frank S Chen
(74) *Attorney, Agent, or Firm* — Olive Law Group, PLLC

(57) ABSTRACT

Systems and methods for psycho-signal processing. According to an aspect, a method includes receiving a visual representation of a subject. The method also includes performing a structured motion operation on the received visual representation to generate a modified visual representation of the subject. The method further includes presenting, via a user interface, the modified visual representation.

17 Claims, 10 Drawing Sheets

(51) Int. Cl.
   *G06T 5/00*       (2006.01)
   *A61F 2/48*       (2006.01)

(56)          References Cited

U.S. PATENT DOCUMENTS

2014/0249395 A1   9/2014   Zhou et al.
2015/0235427 A1   8/2015   Nobori et al.
2016/0042501 A1   2/2016   Huang et al.
2016/0302661 A1   10/2016  Alberts et al.

OTHER PUBLICATIONS

International Preliminary Report on Patentability and Written Opinion issued in PCT Application No. PCT/US2018/14756 dated Jul. 23, 2019 (eleven (11) pages).

* cited by examiner

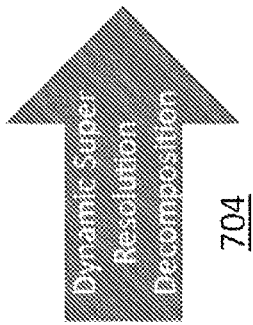
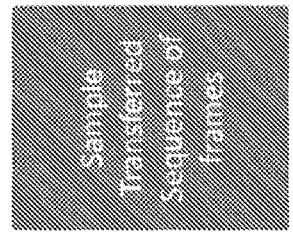
FIG. 7

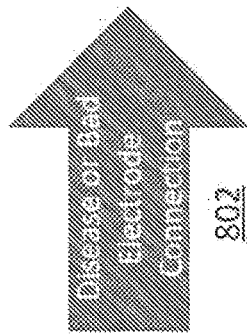
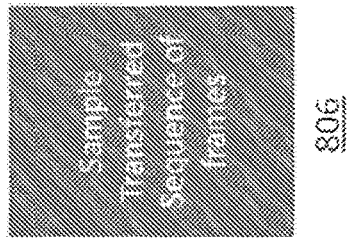
FIG. 8

SYSTEMS AND METHODS FOR PSYCHO-SIGNAL PROCESSING

CROSS REFERENCE

This is a 371 national stage patent application, which claims priority to PCT International Patent Application No. PCT/US2018/014756, filed Jan. 23, 2018, and titled SYSTEMS AND METHODS FOR PSYCHO-SIGNAL PROCESSING, which claims the benefit of the U.S. Provisional Application Ser. No. 62/449,192 filed on Jan. 23, 2017 and titled PSYCHO-SIGNAL PROCESSING SYSTEMS AND METHODS OF USING SAME, the disclosures of which are incorporated herein by reference in their entireties.

TECHNICAL FIELD

The presently disclosed subject matter relates to a signal processing technique for improving vision of patients who use visual aids. More particularly, the presently disclosed subject matter relates to systems and methods for psycho-signal processing.

BACKGROUND

Photoreceptor degenerative diseases are the leading cause of blindness in the elderly in United States. Recent advances in the development of bionic eyes have provided some visual function to blind patients. In bionic eyes, an externally-worn camera captures images from the field-of-view. These images are transferred to a microprocessor that compresses the camera's information and converts the data to electronic signals, which are then transmitted to an implantable retinal prosthesis. The image resolution experienced by these patients is limited by the number of implanted electrodes on the retina, which are analogous to camera charged coupled device (CCD) pixels. To improve the resolution for these patients, more electrodes have to be implanted. This is not a viable solution because the amount of electrodes that can be implanted is limited due to the limited space on the prosthesis as well as on the patient's eye. As such, another solution is needed that can allow for improved resolution in bionic eyes and other visual aids without the need for hardware modification such as increasing the number of implanted electrodes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are systems and methods for psycho-signal processing. According to an aspect, a method includes receiving a visual representation of a subject. The method also includes performing a structured motion operation on the received visual representation to generate a modified visual representation of the subject. The method further includes presenting, via a user interface, the modified visual representation.

BRIEF DESCRIPTION OF THE DRAWINGS

The foregoing summary, as well as the following detailed description of various embodiments, is better understood when read in conjunction with the appended drawings. For the purposes of illustration, the drawings show exemplary embodiments; however, the presently disclosed subject matter is not limited to the specific methods and instrumentalities disclosed. In the drawings:

FIG. 7 is an example of dynamic super-resolution decomposition for systems and methods for psycho-signal processing in accordance with embodiments of the present disclosure;

FIG. 8 is an example of motion-based inpainting process for systems and methods for psycho-signal processing in accordance with embodiments of the present disclosure;

DETAILED DESCRIPTION

Figure 1:
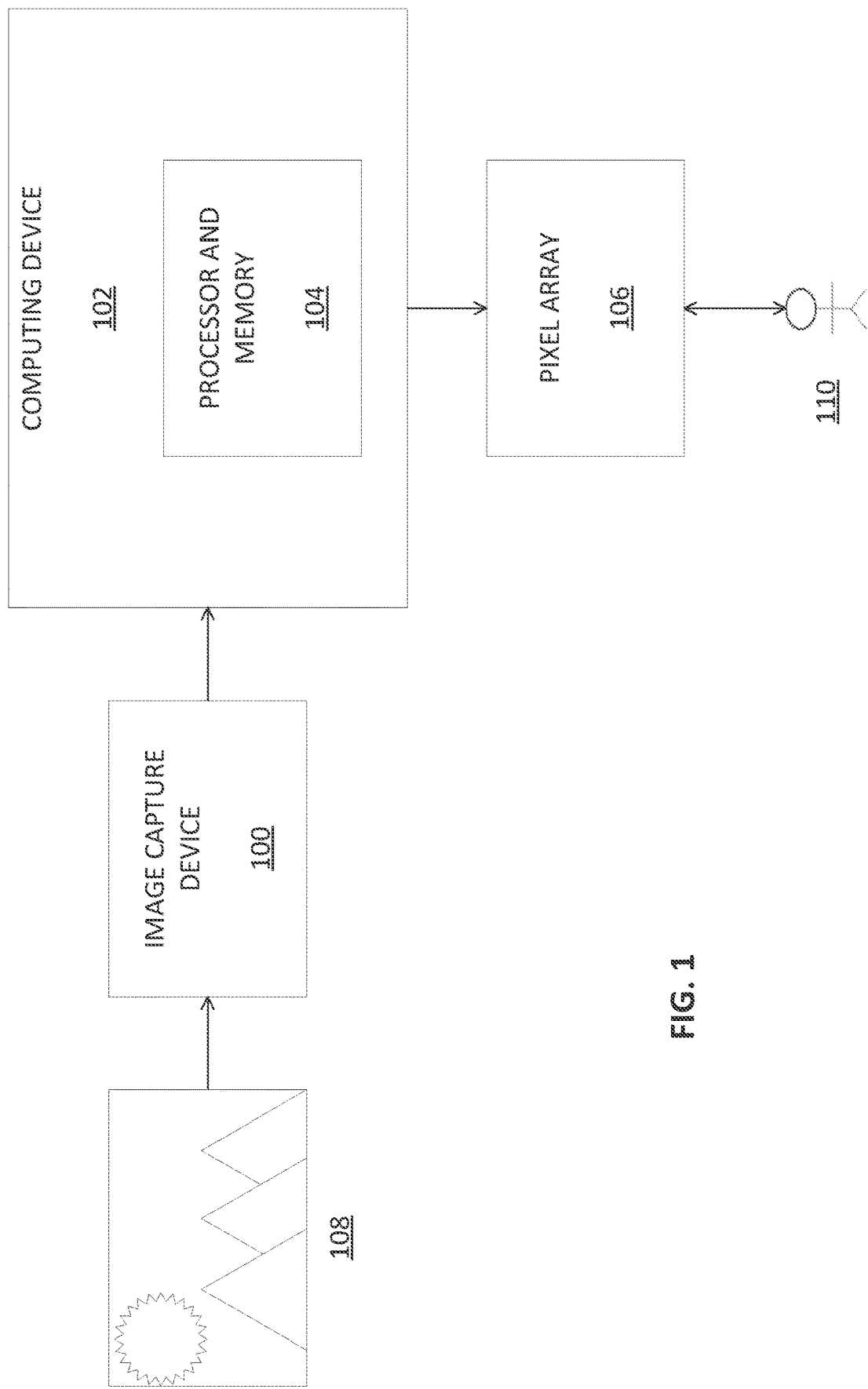
FIG. 1 is a block diagram of an example system for systems and methods for psycho-signal processing in accordance with embodiments of the present disclosure.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

The present disclosure relates to providing signal processing techniques that can provide improved resolution for visual aids, such as bionic eyes, that are used by patients with various visual impediments. This disclosure seeks to improve the vision outcome of patients with implanted retinal prostheses through software to eliminate the need for tedious and costly hardware modifications. As such, the mathematical and psycho-visual foundations can be used in designing these techniques, wherein such foundations take advantage of the brain's image-fusion and enhancement processes.

The advent of bionic eyes has provided some visual function to patients, who were completely blind due to, for example, retinitis pigmentosa and other retinal degenerative diseases prior to implantation of the bionic eyes. In bionic eyes, an externally-worn camera captures images from the field-of-view. These images are transferred to a microprocessor that compresses the camera's information and converts the data into electronic signals, which are then transmitted to a visual aid, such as an Implanted Retinal Prostheses (IRP). However, the image resolution experienced by these patients is currently critically limited by the number of implanted electrodes on the retina, as each electrode produces a single spot of light (phosphene) in the visual field. As such, patients 108 see just flashes of light in their field-of-vision, which can result in a convoluted version of the real world.

Visual information compression is essential as the camera has many more pixels than the electrode array in the implantable retinal prosthesis. That is, the image resolution experienced by these patients is limited by the number of electrodes implanted on the retina, which are analogous to camera charged coupled device (CCD) pixels. For example, the most advanced FDA approved retinal prosthesis system (Argus® II Retinal Prothesis System) consists of only 64 electrodes (a newer 240-electrode model is in a preclinical trial phase). It has been calculated that for even a very low visual acuity of 20/80, an optoelectronic device with a stimulating density of 2500 pixel/mm$^2$ is desired. To improve the resolution for these patients, more electrodes have to be implanted. This is not a viable solution because the amount of electrodes that can be implanted is limited due to the limited space on the prosthesis as well as on the patient's eye. Therefore, a more viable solution is needed. As such, this disclosure seeks to define the mathematical and psycho-visual foundations required for designing software that takes advantage of the brain's inherent spatio-temporal image fusion abilities. That is, by processing the externally-worn camera's information by, for example, introducing spatial and temporal modulations to the captured images before those images are transferred to the electrodes, it is possible to significantly improve the quality of vision experienced by patients with visual aids, such as implanted retinal prostheses.

This disclosure provides an efficient and cost-effective methodology that can improve the vision outcome of patients with IRP through software because it avoids costly hardware modification. Furthermore, the non-invasive nature of a software approach can be easily adapted for improving the vision of most patients using past, present, and future generations of IRP regardless of the number of implanted electrodes in the visual aids or the manufacturer of the visual aids since hardware modifications can differ between manufacturers. In addition, the information obtained from the present disclosure can help determine the limits of the brain's inherent adaptive image-fusion resolution enhancement capability in normal subjects versus patients with IRP. In addition to the above benefits, the software approach enables increased processor efficiency and speed since algorithms are used to maximize the analysis of incoming image data.

In accordance with the embodiments, the present disclosure provides systems and methods for psycho-signal processing. For example, FIG. 1 is a block diagram of an example system for systems and methods for psycho-signal processing in accordance with embodiments of the present disclosure. Referring to FIG. 1, the system includes an image capture device 100, a computing device 102 that may comprise a processor and memory 104, and a pixel array 106. The computing device 102 may be any suitable computer such as a laptop computer, a tablet computer, or a desktop computer. In another example, the computing device 102 may be a mobile computing device. In yet another example, the computing device 102 may be a battery powered Internet of Things (IoT) device. In an example, the image capture device 100 may be a camera, a video camera, or any other suitably similar device that can capture an image 108. The captured image 108 is then sent to the computing device 102 that may comprise a processor and memory 104 for image processing via the methods described in the present disclosure. The processed image is then sent to a pixel array 106 that can be a part of a visual aid, such as an Implanted Retinal Prostheses (IRP), that has been implanted in a patient/person 110. That is, the pixel array 106 can comprise at least one of a visual aid, an electrode, a virtual reality display device, a user interface, and a retinal prostheses implant. As such, the pixel array 106 can be an explicit device (such as a user interface, a monitor, or a virtual reality display device) or an implicit device (such as retinal prostheses implant that can stimulate the patient's 110 brain to create a visual display).

Figure 2:
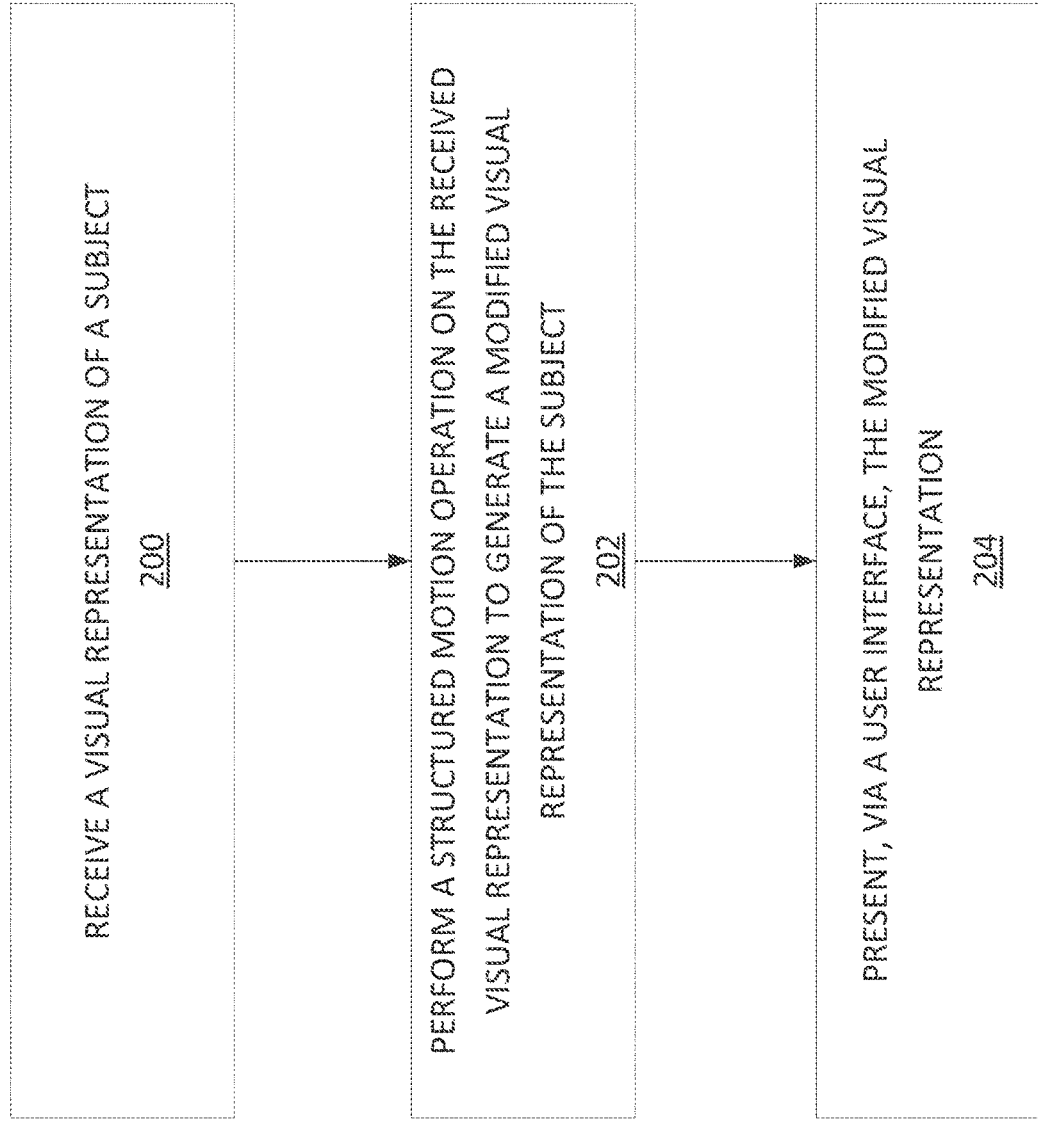
FIG. 2 is a flowchart of an example method for systems and methods for psycho-signal processing in accordance with embodiments of the present disclosure.

FIG. 2 is a flowchart of an example method for systems and methods for psycho-signal processing in accordance with embodiments of the present disclosure. The method of FIG. 2 is described by example as being implemented by the system shown in FIG. 1, although it should be understood that the method may be implemented by any suitable computing device(s) 102 and system(s).

Referring to FIG. 2, the method includes receiving 200 a visual representation 108 of a subject, wherein the visual representation 108 comprises at least one image or video of some subject, such as an image or scenery. The visual representation 108 is received 200 via the image capture device 100, which is then sent to the computing device 102, wherein the processor and memory 104 can perform 202 a structured motion operation on the received 200 visual representation to generate a modified visual representation of the subject. The modified visual representation is then presented 204, via a user interface, such as a pixel array 106 of a patient 110.

Still referring to FIG. 2, in performing 202 the structured motion operation, the computing device 102 can determine a visual acuity measurement of a person 110 in response to viewing the visual representation 108 or another visual representation 108, and from this determination, perform a planned smooth motion operation including panning, blurring, and down-sampling on the received visual representation 108 based on the person's visual acuity measurement in response to viewing the visual representation 108. That is, the structured motion operation can comprise of the planned smooth motion operation that is based on a person's visual acuity measurements as the person views an image of interest or a test image used to gauge the person's visual acuity. In an example, visual acuity measurements may include measuring the person's nerve fiber layer (NFL) or ganglion cell & inner plexiform layer complex (GCCL) using interoperative optical coherence tomography (OCT) of a person with IRP. These measurements can be correlated to determine if the person can demonstrate any visual function improvements.

Alternatively, in performing 202 the structured motion operation, the computing device 102 could also determine an average response of a plurality of people to viewing the visual representation 108 or another visual representation 108. From this average determination, perform a smooth motion operation including panning, blurring, and down-sampling on the received visual representation 108 based on the average response. That is, the structured motion operation can comprise of the planned smooth motion operation that is based on an average of various people's visual acuity measurements as they view an image of interest or a test image used to gauge their visual acuity. The visual acuity measurements can be similar to that previously described.

Still referring to FIG. 2, performing 202 the structured motion operation comprises applying at least one of a dynamic super-resolution decomposition process and a static super-resolution decomposition process to the visual representation 108. That is, performing 202 the structured motion operation comprises using a real-time visual representation processing algorithm that includes at least one of an image segmentation process, an image registration process, an inpainting process, a super-resolution process, and an image decomposition process. This may be done by determining psycho-physically relevant values for use in the real-time visual representation processing algorithm. Further, the real-time visual representation processing algorithm comprises estimating and compensating for temporal motion of objects of interest identified within the visual representation 108. The image segmentation process of real-time visual representation processing algorithm comprises detecting continuous edges of large objects within the visual representation 108 and excluding edges of small features within the visual representation 108. Moreover, various input parameters can be optimized for use in the real-time visual representation processing algorithm, wherein the parameter comprises at least one of a motion smoothness parameter, a frame-rate parameter, a delay parameter between an aliased information to generate a composite low-resolution video sequence of the visual representation, and a point spread function.

Still referring to FIG. 2, the modified visual representation, as obtained from performing 202 the structured motion operation is then presented 204, via a user interface, such as a pixel array 106 to a person 110. Presenting 204 the modified visual representation comprises transferring a composite, low-resolution video sequence of the modified visual representation to at least one of retinal prostheses and a visual aid for a person 110 to mentally fuse the video sequence into a high-resolution visual perception of the subject. Generating the composite, low-resolution video sequence can be achieved by use of, for example, a technique comprising an inverse of a Kalman Filter dynamic super-resolution algorithm.

As previously mentioned, an objective of this disclosure is to define the mathematical and psycho-visual foundations required for designing software that takes advantage of the brain's inherent spatio-temporal image fusion abilities, i.e. the brain's inherent super-resolution (SR) abilities. The real-time visual representation processing algorithm can automatically analyze the dynamic structure of the visual representation of the natural world as captured by the image capture device 100, such as a digital camera; detect the visual representation's 108 most important features; simplify them; and then compress them into an aliased video sequence with smooth motion, with the video sequence being suitable for enhancement by the brain's inherent super-resolution abilities. This can be analogous to the inverse of the computer (artificial) super-resolution methodology. That is, instead of using an extra computer to fuse aliased low-resolution (LR) images to create a high-resolution (HR) image, the algorithm can deconstruct each HR image into a series of P aliased LR images with the exact number of pixels in the visual aid itself, such as the implanted retinal electrodes. For example, let us say that each HR frame is broken into four LR images (P=4). In this case, if the image capture device's 100 HR frame rate is 15 Hz, then the resulting LR video frame rate will be 60 Hz. In practice, an image capture device's 100 resolution is thousands of times higher than the resolution of the implanted electrodes. This property gives us the opportunity to select a subset of synthetic LR frames that when played sequentially shows a smooth non-vibrating transition between frames. We can transfer a stream of such video sequences at, for example, a minimum of 60 frames per second (fps) to a pixel array 106, such as a retinal prosthesis to allow the patient's 110 brain function to fuse these video sequences into a HR video.

Mathematically speaking, to accommodate an [M×M] array of, for example, retinal electrodes, we define the state-space forward model of our imaging modality (a generalization of the SR concept described in FIG. 4 below) as:

$$\begin{cases} x_k = F(w_{k,k-1})x_{k-1} + u_k & (1) \\ y_{k,p} = DHS(v_{k,p})x_k + e_{k,p}, & p \in \{1, 2, \ldots, P\} \end{cases}$$

In this formula, the [N×N] pixels HR image, captured by, in an example, the digital camera 100 at time k, is represented by the lexicographically ordered vector $x_k$ (size [$N^2 \times 1$]). Equation (1) states that up to some innovation content $u_k$, the current HR image ($x_k$) is a geometrically warped version of the previous image, $x_{k-1}$. The matrix $F(w_{k,k-1})$ of size [$N^2 \times N^2$] represents the warping operator (encoding motion) between two consecutive HR images from the camera 100. The so-called system noise $u_k$ is assumed to be additive zero-mean Gaussian. In equation (2), the transmitted [M×M] LR image at time point k+p−1 vectorized in the lexicographic order (size [$M^2 \times 1$]) is represented by $y_{k,p}$, where (M<<N). Matrix D of size ([$M^2 \times N^2$]) represents the downsampling operation and H of size ([$N^2 \times N^2$]) represents the system's space variant point spread function (PSF), in the form of visualized phosphenes. $S(v_{k,p})$ is the warping operator of size [$N^2 \times N^2$] representing the subpixel spatial shifts between similar tiles in the LR images (dense motion), and $e_{k,p}$ represents the residual error (size [$M^2 \times 1$]) resulting from non-integer shifts in $S(v_{k,p})$ and quantization, which is modeled as a zero-mean Gaussian random process.

To obtain psycho-physically relevant values for $y_{k,p}$, we will determine the appropriate values for F, D, H, and S based on a mathematical approach to minimize a global notion of $e_{k,p}$ and $u_k$ in concert with the physical characteristics of, for example, the retinal prosthesis as well as the brain's image fusion constraints and properties. More specifically, in the software experiment phase, as subsequently described, we can use, for example, the Simulator (v. 2.0) software and its parameters, as developed by Second Sight™, to simulate the visual experience of patients with IRP in normal subjects. We will utilize this software's phosphene vision model as the pilot estimate of the point spread function (H). From this simulation, we can then determine improvements for a specific patient by selecting an H value that provides the most appealing vision for each specific patient with IRP. The elements and dimensions of matrix D are determined based on the number of the electrodes in, for example, the retinal prosthesis and the number of pixels in, for example, the digital camera 100.

During the patient experiment phase, as subsequently described, if post implantation visual tests determine non-functioning electrodes in a patient with IRP, the values of the corresponding row in D will be replaced with zeros for that patient (similar to the case of missing pixels in artificial SR). Elements of matrix F are selected directly from the motion estimation process between two consecutive HR images from the image capture device 100, such as a camera. However, S's elements will be chosen so that mainly the most important features in the camera's 100 HR image are sampled and ignoring the less informative pixels. For example, where a visual representation 108 is of a moving vehicle, only every other pixel on the edges of a moving vehicle are selected in one frame, followed by selecting the neighboring pixels at the next time point. As such, the mathematical methods and software is developed in conjunction with the patient experiment phase to obtain the best results for patients suffering from visual impairments.

As previously mentioned, the enhanced data compression is obtained by detecting and transferring the most important (i.e. informative) features seen in the HR images ($x_k$). The real-time visual representation processing algorithm is used to detect continuous edges in $x_k$. Novel graph theory based ideas are used to selectively exclude edges corresponding to small features and instead focus on the edges of larger objects, especially those with onward motion (e.g. an approaching vehicle). This enables the development of automatic image segmentation process of the features of interest in a visual representation 108, as captured by the image capture device 100, such as a digital camera.

Figure 3:
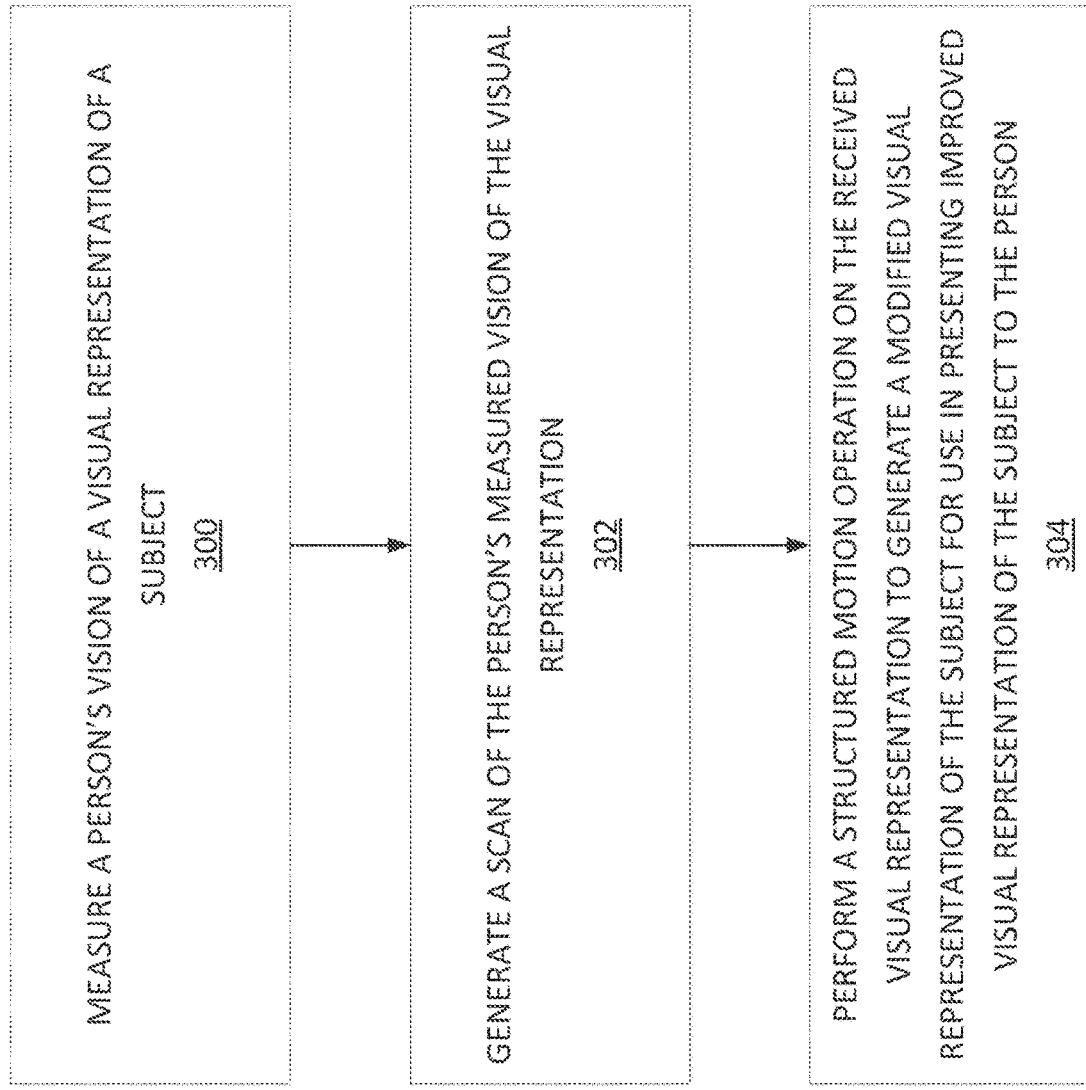
FIG. 3 is a flowchart of an example deconvolution method for systems and methods for psycho-signal processing in accordance with embodiments of the present disclosure.

FIG. 3 is a flowchart of an example deconvolution method for systems and methods for psycho-signal processing in accordance with embodiments of the present disclosure. The method of FIG. 3 is described by example as being implemented by the system shown in FIG. 1, although it should be understood that the method may be implemented by any suitable computing device(s) 102 and system(s).

Referring to FIG. 3, the method includes measuring 300 a person's vision of a visual representation 108 of a subject, wherein the visual representation 108 comprises at least one image or video of some subject, such as an image or scenery. The method also includes generating 302 a scan of the person's measured vision of the visual representation 108. The method further includes performing 304 a structured motion operation on the received visual representation 108 to generate a modified visual representation of the subject for use in presenting improved visual representation of the subject to the person 110.

In generating 302 the scan of the person's measured vision of the visual representation 108, the scan is optimized based on at least one of a person's 110 visual acuity measurement to the visual representation 108 and an average response of a plurality of people 110 to viewing the visual representation 108. That is, the measured vision can be based on a person's visual acuity measurements as the person views an image of interest or a test image used to gauge the person's visual acuity. In an example, visual acuity measurements may include measuring the person's nerve fiber layer (NFL) or ganglion cell & inner plexiform layer complex (GCCL) using interoperative optical coherence tomography (OCT) of a person with IRP. These measurements can be correlated to determine if the person can demonstrate any visual function improvements. Hence, a determination of the visual acuity measurement of the person can be achieved based on feedback from the person upon viewing the visual representation 108 and from this feedback, determine one or more aberrations in the person's 110 eyesight based on the visual acuity measurement.

In an example, a patient 110 has a visual aberration wherein he sees a convoluted version of the real world. As such, a visual acuity measurement has to be made so that the visual aberration can be determined. Using this determination, a modified convoluted visual representation can be generated based on the scan of the person's 110 measured vision of the visual representation 108. Then, this modified convoluted visual representation can be presented back to the patient 110 via a pixel array 106. Since the patient has the visual aberration, he can then re-convolve the modified visual representation to generate a corrected visual representation of the real world. That is, the modified visual representation is re-convolved to generate a corrected visual representation for the person.

Still referring to FIG. 3, in performing 304 the structured motion operation, the computing device 102 can determine a visual acuity measurement of a person 110 in response to viewing the visual representation 108 or another visual representation 108, and from this determination, perform a planned smooth motion operation including panning, blurring, and down-samplling on the received visual representation 108 based on the person's 110 visual acuity measurement in response to viewing the visual representation 108. That is, the structured motion operation can comprise of the planned smooth motion operation that is based on a person's 110 visual acuity measurements as the person views an image of interest or a test image used to gauge the person's 110 visual acuity. In an example, a patient 110 can have an electronic pen to draw what they are seeing in order to gauge their visual acuity, i.e. aberration due to seeing a convoluted version of the real world.

Alternatively, in performing 304 the structured motion operation, the computing device 102 could also determine an average response of a plurality of people to viewing the visual representation 108 or another visual representation 108. From this average determination, perform a smooth motion operation including panning, blurring, and down-sampling on the received visual representation 108 based on the average response. That is, the structured motion operation can comprise of the planned smooth motion operation that is based on an average of various people's visual acuity measurements as they view an image of interest or a test image used to gauge their visual acuity. The visual acuity measurements can be similar to that previously described.

Still referring to FIG. 3, performing 304 the structured motion operation comprises applying at least one of a dynamic super-resolution decomposition process and a static super-resolution decomposition process to the visual representation 108. That is, performing 304 the structured motion operation comprises using a real-time visual representation processing algorithm that includes at least one of an image segmentation process, an image registration process, an inpainting process, a super-resolution process, and an image decomposition process. This may be done by determining psycho-physically relevant values for use in the real-time visual representation processing algorithm. Further, the real-time visual representation processing algorithm comprises estimating and compensating for temporal motion of objects of interest identified within the visual representation 108. The image segmentation process of real-time visual representation processing algorithm comprises detecting continuous edges of large objects within the visual representation 108 and excluding edges of small features within the visual representation 108. Moreover, various input parameters can be optimized for use in the real-time visual representation processing algorithm, wherein the parameter comprises at least one of a motion smoothness parameter, a frame-rate parameter, a delay parameter between an aliased information to generate a composite low-resolution video sequence of the visual representation, and a point spread function.

Still referring to FIG. 3, the modified visual representation, as obtained from performing 304 the structured motion operation is then presented, via a user interface, such as a pixel array 106 to a person 110. Presenting the modified visual representation comprises transferring a composite, low-resolution video sequence of the modified visual representation to at least one of retinal prostheses and a visual aid for a person 110 to mentally fuse the video sequence into a high-resolution visual perception of the subject. Generating the composite, low-resolution video sequence can be achieved by use of, for example, a technique comprising an inverse of a Kalman Filter dynamic super-resolution algorithm.

To estimate and compensate for the temporal motion for objects of interest in a visual representation 108, we note that the brain's hyper-acuity capability is optimal when moving objects have a smooth non-vibrating transition. As such, this allows us to provide automatic motion estimation via the real-time visual representation processing algorithm. To do so, we note that the overall motion experienced by the patient is a combination of two distinct types of motion: real and unknown (F) and synthetic and known (S). To estimate (F), we will extend and utilize the fast and accurate block-based joint motion estimation algorithm. In this algorithm, we will break the received visual representation 108 into smaller, optimal-sized blocks, each with an assumed independent motion. Utilizing the concept of variable projections, we can develop an efficient and fast Fourier domain based algorithm to estimate the respective motion of the smaller, optimal-sized blocks. To replace the cumbersome region-of-interest wherein the patient is manually scanning the field of vision to see better, we will add a fixed number of shifts to the estimated motion to replicate the scanning process through software (parameters to be set based on experimentation). By low-pass filtering the overall motion $(S(v_{k,p}) \times F(w_{k,k-1}))$ in the LR video, we can remove the vibrations and attain smooth motion for each object. That is, obtain structured motion.

To generate a composite HR video in the brain of a patient 110, we will estimate the most appropriate series of spatially aliased LR images that are transferred to the pixel array 106, such as the implanted electrodes, in rapid succession in order to generate a composite HR video in the brain. This can be achieved using a technique which is the inverse of a Kalman Filter dynamic SR algorithm. Based on the patient experiment phase, we can determine the maximum number of frames (P) that can be utilized by patients 110 to experience the natural SR phenomenon and the overall temporal distance between them. Then, for the first transmitted frame, we can down-sample the features detected in the previously captured HR images. The combined motion and point spread function matrices can be determined by optimizing a least squares cost function with a smoothness prior, which minimizes the effect of $e_{k,p}$ and $u_k$ in the past P frames (i.e. $L_2$ norm likelihood term with Tikhonov regularization technique prior). After this initial frame, the successive frames are determined in a computationally efficient manner via the Kalman Filtering approach. Further, since filtered (for e.g. Lanczos2 filtering technique) version of a camera's 100 images provide better visual acuity for IRP patients, we can repeat these experiments by utilizing filtered images and compare the results of the filtered with the unfiltered images.

Software Experiment Phase

The aim of this is to develop user-friendly software that executes the real-time visual representation processing algorithm. The various algorithms used are suitable for parallel processing. In an example, a high-performance NVIDIA GPU can be used and programmed using the CUDA parallel platform. This can then be incorporated into our system 102 to significantly accelerate the execution of our algorithm, such as the segmentation process, the registration process, and the deconstruction process of the algorithm.

Patient Experiment Phase

The aim of this is to perform pilot experiments to provide feedback on the system 102 design and assess the effectiveness of the proposed modulation technique for improving the visual experience via psychophysical testing of healthy adult subjects and patients with, for example, implanted retinal prostheses.

Part 1: Experiment on Healthy Adult Subjects Equipped with Devices that Mimic Bionic Eyes The aim of this is to test and optimize the effectiveness of the visual representation 108 manipulations for improving visual performance.

Approach: The goal is to develop improvements in the visual acuity of patients with IRP, yet in the first phase it is premature to test (or debug) these algorithms in such vulnerable patients. Fortunately, much can be learned from testing healthy human subjects, simulating the conditions likely to be experienced by IRP recipients. This can be done via specific manipulations of the camera image to electrode mapping. In this aim, we can conduct psychophysical testing to determine how such image manipulations can improve performance in visual detection and identification tasks. To make the task experience similar to that of patients with IRPs, retinal stabilization of images will be used while the eyes are near the center of the oculomotor range. Subjects can perform a battery of standard visual psychophysical tasks including orientation discrimination, contrast detection, and visual search. We can then compare the performance using non-manipulated LR images to the performance using manipulated images. These studies have can help determine input parameters to optimize for normal subjects prior to experiments involving implant recipients. Such input parameters to optimize may include: a) motion smoothness, b) frame-rate, c) delay between aliased information (in micro-seconds) which can be utilized for generating a composite HR image in the brain, and d) point spread function.

Experimental Logistics: Separate experiments can be implemented for each parameter to systematically determine its added benefit. Instructions and practice trials can be administered before the approximately one-hour testing session. Half the number of volunteer subjects should female, while the remaining half should be male. The required number of participants for high statistical power are estimated by Mead's resource equation as N=E+B+T where E=20 (threshold for high power), B=0 (no complicating factors such as stratified design), and T=5 (3 tasks each with their own control conditions, minus 1). N=25 should therefore be adequate, or 27 to allow for equal numbers (N=9) for each task. In psychophysical experiments, subject data are sometimes unusable, for e.g. if a subject stops the experiment early, so as an extra assurance of power, we can double the minimum N=9, leading to a final planned N=18 subjects/experiment. This number of subjects is 50% over the N=12 standard that we have found to yield unambiguous results previously. Aside from reporting the results for all 54 subjects, we can also perform and report all analysis for each gender separately. Age might be found to be a slight biological variable for very old subjects. Thus, it can be considered in future larger studies. Other variables such as weight are not expected to affect the brain's SR capabilities.

Experimental Design: we walk through one example study here that is representative of the planned testing. The goal of this experiment is to determine the most efficient algorithm for detecting edges. Several different algorithms can be implemented with each producing a unique set of edge representations. These output representations can then serve as the stimuli for behavioral psychophysical experiments. Three conventional experimental designs (orientation discrimination, contrast detection, and visual search) can be used to converge on the best algorithm. For brevity, we describe here one task, an orientation discrimination experiment. In this task, subjects are instructed to look at the center of a computer monitor. There will be no requirement to foveate a "fixation point" because that is challenging for patients with IRPs. When the eyes are within, for example, 3 degrees of center, a retinal stabilization technique (i.e. a real-time tracking of eye position to control image presentation on a, for example, 200 Hz monitor) can be used to present peripheral images. Two rectangles with distinct edges will appear on each trial, to the right and left of fixation. Subjects will simply report, by key press, whether the rectangles are oriented in the same direction or not. The orientations will vary sufficiently to generate psychophysical curves as a function of angular difference, including catch trials with no difference, with performance measured and denoted as d'. This takes into account correct, false alarm, and correct rejection reports. The contrast detection task will be similar in design but require detection of a single stimulus (such as a Gabor patch) of varying contrast appearing randomly to the left or right. The visual search task will be similar but require the discrimination of featural and motion differences between stimuli consisting of natural objects (for e.g. images of apples that vary in hue if stationary, or speed if translating or rotating). The critical manipulation in the experiments is that the stimuli can be comprised of outputs from the various tested algorithms, which can vary across trials with, for example, 50 trials for each of the candidate algorithms developed above. This is used to determine which algorithm produces the best visual sensitivity (d') across the visual challenges of detecting edge orientation, contrast, features, and motion.

Part 2: Experiment on Patients with Implanted Retinal Prostheses

The aim of this experiment is to assess the software's performance in improving the visual acuity of patients with IRP.

Approach: modify the information processing pipeline and the camera's video output in Argus® II Retinal Prosthesis System to match the algorithm found to give the best visual sensitivity. Once this offline system adaptation is perfected, we can recruit patients with Argus® II implants.

We can perform the same battery of tests as described above to set a baseline. In general, the extent of the surviving ganglion cells is a factor in the visual experience of patients with IRP. However, in target patients, the inner retinal cells (for e.g. bipolar, horizontal, amacrine and ganglion cells) and nerve fiber layer (NFL) remain largely preserve. In fact, the patients' visual acuity as a surrogate for functional ganglion cells are usually tested in great detail as part of routine eligibility screening for these patients. Thus, these patients have significantly more ganglion cells than implanted electrodes, facilitating implementation of our algorithm. However, since we have access to the intraoperative optical coherence tomography (OCT) of these patients before, during, and after implant surgery, we can measure and correlate the thicknesses of the NFL and ganglion cell & inner plexiform layer complex (GCCL) with the vision improvement after implantation both with and without utilizing our SR approach. Accurate placing of electrodes on the raphe and much closer to retinal surface (by utilizing intraoperative OCT) in recent years has resulted in significantly lower warping experienced by the patients. However, in the event that the vision experienced by some of patients appear to be in the form of elongated, warped, or streaked phosphenes, we can follow the approach of utilizing, for example, touch screens to map the experienced visualization of the electrode response in order to better utilize the power of SR technique. This constitutes a classic forward image synthesis problem. That is, in an iterative approach, we systematically modify the input (as the continuous analogues by modifying matrix H of Eq. 2) such that it compensates for these imaging artifacts.

While nystagmus can reduce the quality of OCT images in some subjects, this will not be an issue, because we can utilize the intraoperative OCT system at our facility that can better image anesthetized patients pre, intra, and post implantation as routinely done. Even without intraoperative OCT, lower-quality images with motion can be corrected in postprocessing, as well.

Figure 4:
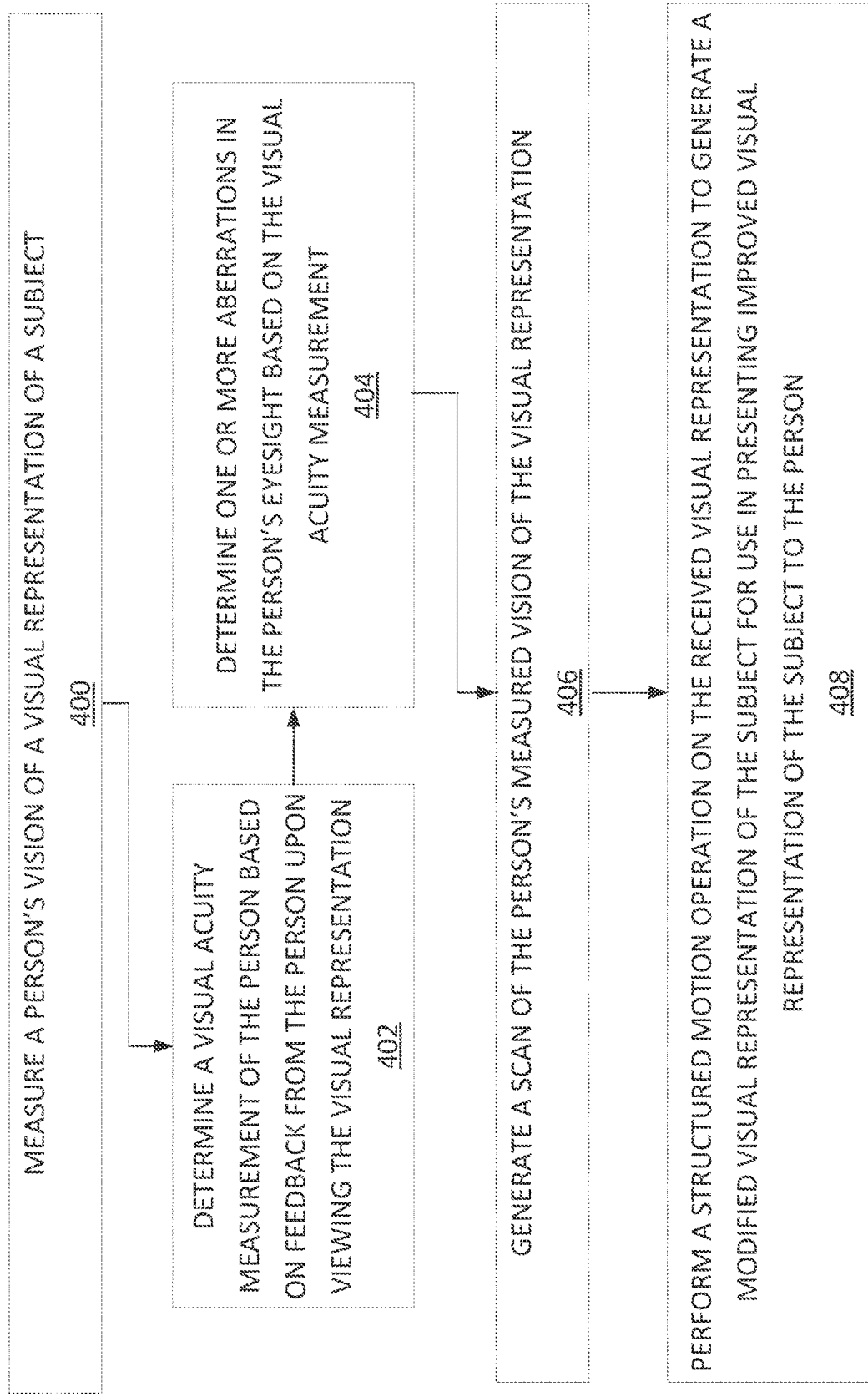
FIG. 4 is a flowchart showing an example deconvolution method and determining a person's visual acuity for systems and methods for psycho-signal processing in accordance with embodiments of the present disclosure.

Returning now to the figures, FIG. 4 is a flowchart showing an example deconvolution method and determining a person's visual acuity for systems and methods for psycho-signal processing in accordance with embodiments of the present disclosure. Similar to FIG. 3, the method of FIG. 4 includes measuring 400 a person's vision of a visual representation 108 of a subject. The method then expands on the measuring 400 step by showing measuring 400 comprises determining 402 a visual acuity measurement of the person based on feedback from the person upon viewing the visual representation and determining 404 one or more aberrations in the person's eyesight based on the visual acuity measurement. From there, the method includes generating 406 a scan of the person's measured vision of the visual representation. The method further includes performing 408 a structured motion operation on the received visual representation 108 to generate a modified visual representation of the subject for use in presenting improved visual representation of the subject to the person 110.

Figure 5:
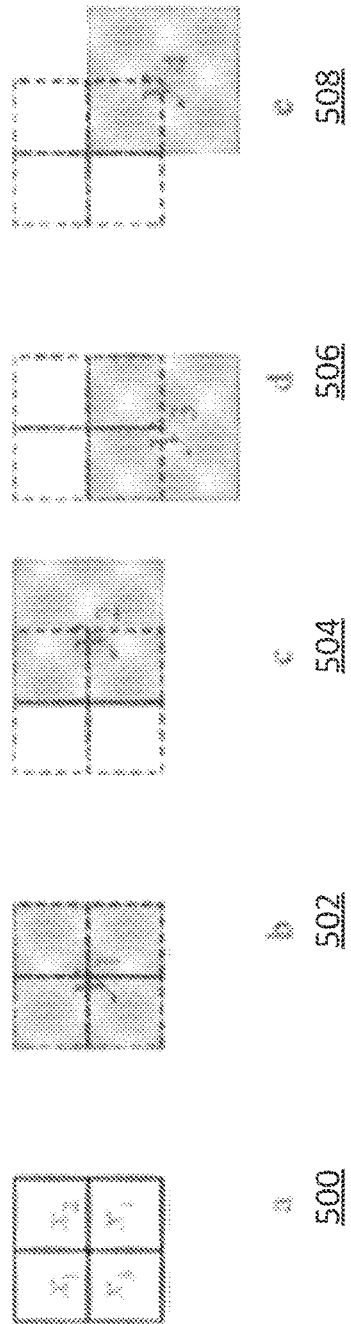
FIG. 5 is an example of motion-based artificial super-resolution for systems and methods for psycho-signal processing in accordance with embodiments of the present disclosure.

FIG. 5 is an example of motion-based artificial super-resolution (SR) for systems and methods for psycho-signal processing in accordance with embodiments of the present disclosure. In (a), a high-resolution (HR) image 500 consists of four pixels. In parts (b) to (e), low-resolution (LR) images 502, 504, 504, 506 and 508 are obtained via moving an image capture device 100, such as a single pixel camera. Assuming that the camera's 100 point spread function (PSF) is known and the gray level of all bordering pixels is zero, the pixel values of the high-resolution image can be precisely estimated from the LR images by solving the set of linear equations 510, in which $y_i$ and $e_i$ represent the $i^{th}$ LR image and noise, respectively. $x_i$ and $h_i$ represent the $i^{th}$ pixel in the high-resolution image and PSF, respectively. Indeed, in practice, the motion, boundary values, and PSF are estimated along with the high-resolution measurement.

To understand the concepts described subsequently in FIG. 6 to FIG. 9, we first present a background on artificial super-resolution (SR) and natural super-resolution (SR).

Artificial Super-Resolution

The problem of limited functional vision due to a low number of, for example, electrode implants resembles the problem of acquiring low-quality (aliased) images from an image capture device 100, such as cameras with small number of CCD pixels. To address the image quality issue in digital cameras 100, a collection of algorithms known as super-resolution (SR) for generating high-resolution (HR) imagery from systems having lower-resolution (LR) imaging detectors. These algorithms combine a collection of LR images with aliasing artifacts to restore a HR image, as shown in FIG. 5. The ability to transcend the fundamental resolution limits of sensors using SR algorithms (without any change in sensor hardware) has greatly improved the quality of photographic imaging. Traditional SR techniques create a single HR image output, while we propose a technique of fusing a streaming LR video input to create a streaming HR video quality output, virtually in real time, with the same frame rate as the input video. This can provide an economic solution for greatly improving visual capabilities in patients 110 with vision conditions.

Natural Super-Resolution

Interestingly, nature has adapted to create its own version of super-resolution. For example, the retinal movements of jumping spiders allow them to have a perceived resolution far beyond their limited 1600 photoreceptors. It is has been suggested that the human visual system exploits similar micro movements of the eye to visualize objects beyond the Nyquist limit, which dictated by the number of photoreceptors in the retina. Note that, unlike computerized SR, the human visual system might not literally reconstruct a HR image, rather these micro movements allow for a finer localization of edges, which is may be the same as SR, to some extent. Note also that, the natural SR ability in the human eye is functional only under certain conditions. That is to say, it is fairly limited. For example, while it seems that our eye is able to super-resolve a smoothly moving object, it can lose track of objects which vibrate fast. Moreover, it is shown that fixational eye movements via equalizing spatial energy across the temporal domain can account for improvements in perceived contrast of images that are resolvable by the eye's cone mosaic. Therefore, one aim of this disclosure is to better understand and utilize the natural SR ability (both below and above the Nyquist limit) so that it can be incorporated into, for example, a retinal prosthesis design to improve the visual acuity of patients 108 with IRP.

Still examining natural SR, a basic preliminary experiment has confirmed that the human brain takes advantage of similar SR processes to create high-quality images from moving objects. In this preliminary experiment, we selected a real-world video sequence for SR experimentation. In this sequence, a video camera captures images from the license plate of a moving car. We found that when the video is played at the rate of 10 frames per second (fps), the aliasing artifacts in these LR frames make the license plate numbers unrecognizable. However, when we play this video at the rate of 60 fps (with similar spatial resolution), our brain can automatically super-resolve the information of consecutive frames, enabling the license plate to become readable. Such natural SR algorithms can be mimicked by the artificial SR image reconstruction algorithm, i.e. fusing information of several LR images in a post-processing step to create an image with three times higher spatial resolution in each direction. This preliminary experiment showed a visual real-world proof-of-concept experience of the SR phenomenon. However, the visual experience of the patients with retinal prosthesis is more limited. As such, this disclosure provides an artificial SR process that can assist these patients. Furthermore, humans' ability to construct and process SR is limited. To better assist these patients, additional modeling and simulation of the phosphene vision in these patients are performed in the patient experiment phase, as described above.

Our research has shown no demonstrated work on the utilization of SR technology with structured motions as disclosed herein. One important property of the proposed disclosure is that it can be utilized in parallel and even incorporate other image processing algorithms deemed impactful for patients with IRP in conjunction with the real-time visual representation processing algorithm disclosed herein. For example, the edges in the visual representations 108 (or other types of filtering) can provide more information for retinal implanted patients 110 than the visual representations 108 themselves. Thus, we can replace the stream of low-resolution images in our SR algorithm with the filtered/edge detected version, which was previously described in detail. A major difference between our approach as detailed in this disclosure and dithering is that we utilize structured motion rather than random vibrations. This is critical distinction because our disclosure enables a more efficient utilization of the SR vision experience by providing a higher-resolution vision experience. Dithering is a process by which random motion, such as that can occur when an image capture device 100 shakes while capturing the visual representation 108, can provide an improved resolution due to the random motion of the shaking. This is not ideal because the brain cannot predict such random motion, so is not able to take advantage of to obtain better vision. In other words, random motion is, by definition, random and thus unreliable. As such, a patient's eye cannot construct such motion in any fashion in order for the brain to take advantage of this. Thus, our disclosure provides a novel means to create structured motion, i.e. smooth motion as previously described above, that can provide a continuous means for the brain to obtain improved resolution of images without needing random occurrences to see. Moreover, our structured motion approach obviates the necessity for the sub-optimal manual scanning of the field-of-view by patient's head motion, wherein patients with, for example, a broken electrode in their visual aid must constantly scan their head in order to see the whole field-of-view that can be partially obscured due to the broken electrode. Our disclosure obviates this manual scanning by replacing it with software controlled scanning in a principled manner, as part of the inpainting process of the real-time visual representation processing algorithm. This real-time visual representation processing algorithm may be implemented via, for example, a computer readable storage medium as part of a computing device 102 and its processor and memory 104.

Figure 6:
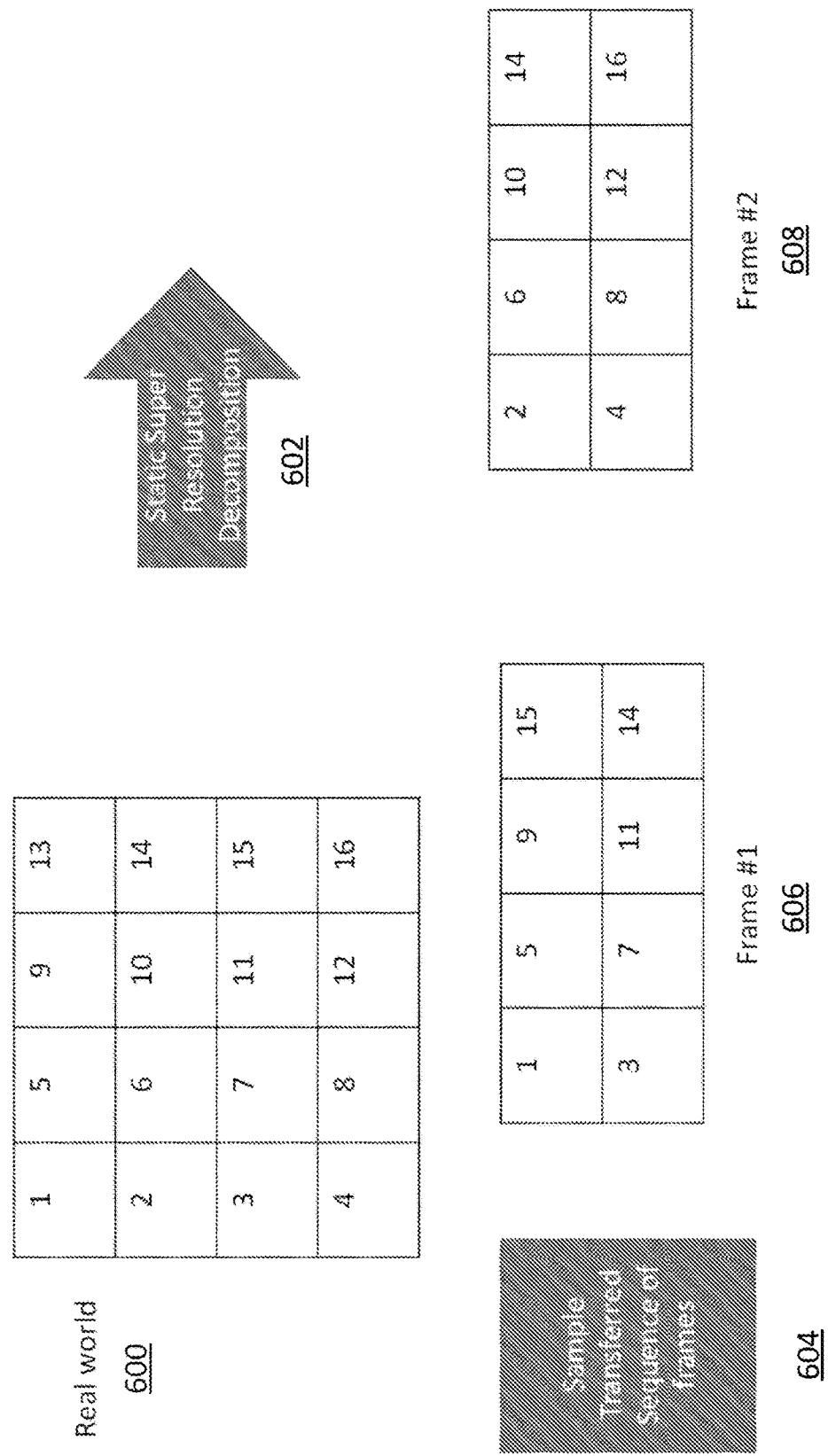
FIG. 6 is an example of static super-resolution decomposition for systems and methods for psycho-signal processing in accordance with embodiments of the present disclosure.

With this background, we now turn back to the figures. FIG. 6 is an example of static super-resolution decomposition 602 for systems and methods for psycho-signal processing in accordance with embodiments of the present disclosure. In this example, for illustration and simplicity, we assume that the patient 108 has an implanted retinal prosthesis with a 4×2 number of electrodes. In reality, patients can have much higher number of electrodes. Furthermore, in this example, we are trying to improve the SR in a downward y-direction. We note that our disclosure provides improvement in both the x and y directions. The real world 600 shows a true state of a visual representation 108. It is what people will normal vision will see. Patients with IRP do not see this. Using static super resolution decomposition 602, we can decompose the real world 600 so that the patients can see properly see it. Decomposition meaning to make low-resolution images. Static super resolution decomposition 602 starts from a singular image for the visual representation 108 and decomposes it to create a video sequence that can be presented 204 to the patient 110 via a pixel array 106 for the patient to fuse into a high-resolution visual perception of the visual representation 108. To do this, a sample transferred sequence of frames 604 must occur. Here, we decompose the real world 600 into frame 1 606 and frame 2 608. This is obtained by passing a low-resolution of the 1$^{st}$ and 3$^{rd}$ row from the real world 600 for frame 1 606, and then passing a low-resolution of the 2$^{nd}$ and 4$^{th}$ rows of the real world 600 for frame 2 608 into the real-time visual representation processing algorithm. The algorithm enables a piecing together of a high-resolution composite that is sent to the pixel array 106. By performing the static super resolution decomposition 602, we have increased the patient's 110 resolution by twofold. Hence, static super resolution decomposition 602 is the case where a lower-resolution video can be created from sub-sampling of a single higher-resolution image/visual representation 108.

FIG. 7 is an example of dynamic super-resolution decomposition 704 for systems and methods for psycho-signal processing in accordance with embodiments of the present disclosure. Similarly, in this example, for illustration and simplicity, we assume that the patient 110 has an implanted retinal prosthesis with a 4×2 number of electrodes. In reality, patients 110 can have much higher number of electrodes. Here, dynamic denotes a video image rather a singular image for the visual representation 108. Thus, the real world is comprised of real world frame 1 700 and real world frame 2 702. The 'e' in real world frame 2 702 denotes an error, i.e. '1+e1' means pixel at location 1 with error 1. This error can due to noise, some motion from the image capture device 100, or some other error that is occurring in the real world. Since this is a dynamic visual representation 108 of the real world, the world is moving and therefore, in this example, the image capture device 100 is moving downward. Using dynamic super resolution decomposition 704, we can decompose the real world frame 1 700 and frame 2 704 so that the patients can see properly see it. Decomposition meaning to decompose the video of the real world into low-resolution videos that will then be presented 204 to the patient 110.

Still referring to FIG. 7, dynamic super resolution decomposition 704 starts with decomposing the visual representations 108 of the real world 700, 702 and decomposing them to create a video sequence that can be presented 204 to the patient 110 via a pixel array 106 for the patient to fuse into a high-resolution visual perception of the visual representation 108. To do this, a sample transferred sequence of frames 706 must occur. Here, frame 1 708 is created in a similar manner to the static process described in FIG. 6, wherein rows 1 and 3 of the real world frame 1 700 are selected. Then, frame 2 710 is created by picking row 3 of the real world frame 2 702 because it is the counterpart to row 2 of the real world frame 1 700. It is the counterpart because we see the same initial pixel values but also the associated errors that can occur due to this being a dynamic visual representation 108. Frame 2 710 also includes row 4 of the real world frame 1 700. Note that there is no counterpart for row 4 of the real world frame 1 700 because the image capture device 100, such as a camera, does not go low enough to capture the counterpart and its corresponding error. This is due to the fact that the camera is moving downwards, and thus the real world frames are rising upwards. As such, real world frame 2 702 only has the counterpart of row 3 in the real world frame 1 700, because that is the lowest row the camera can see from real world frame 1 700. The resulting frames 1 708 and 2 710 are passed into the real-time visual representation processing algorithm. The algorithm enables a piecing together of a high-resolution composite that is sent to the pixel array 106. By performing the dynamic super resolution decomposition 602, we have increased the patient's 110 resolution by twofold. Thus, dynamic super-resolution 704 is the case where a lower-resolution video can be created from sub-sampling of another motion compensated higher-resolution real-time video with a similar or lower frame rate. In dynamic, we are comparing the various motion uncompensated frames with each other.

FIG. 8 is an example of motion-based inpainting process for systems and methods for psycho-signal processing in accordance with embodiments of the present disclosure. Inpainting process is used to counteract patients 110 having to manually scan the scene so that they can get a better field-of-view due the broken electrodes present in their visual implants. In this example, for illustration and simplicity, we assume that the patient 108 has an implanted retinal prosthesis with a 4×2 number of electrodes. In reality, patients can have much higher number of electrodes. The real world 800 shows a true state of a visual representation 108, with a 16 pixel vision. It is what people will normal vision will see. Here, the patient 110 has a diseased or bad electrode connection 802 that results in the patient 110 not being able to see pixel 7, as denoted by the black box. That is, the vision experienced 804 by the patient 110 is blacked out where pixel 7 is located. Hence, pixel 7 does not shoot any electrical pulses that would allow the patient 110 to see. To fix this issue, a patient 110 can scan his head to: (1) improve his field-of-vision to see a larger field or (2) to see the broken pixel location via movement of his head. That is, frame 1 808 is an image of the real world 800 in one instant of time, so if the patient moves his head to the right as he views the real world 800, i.e. from frame 1 808 to frame 2 810, then he can hope to see pixel 7 by this movement. This is because the patient's experienced vision 804 is broken at the location of pixel 7, but by moving his head to the right, the broken location seen also moves, enabling the original pixel 7 to be seen. We can see that in frame 2 810, wherein the original pixel 7 is now visible, while pixel 11 is not because it is now in the location of the original pixel 7, as shown when compared with the experienced vision 804. In this disclosure, we seek to obviate this mechanical motion done by the patient while still obtaining the same result. That is, we replace this manual scanning by a patient's mechanical head motion by performing an implicit scanning of the scene, i.e. visual representation 108, by moving the moving the scene at a predetermined pace for the patient 110. This predetermined pace can be obtained based on: (1) the patient's 110 visual acuity measurement to the visual representation 108 or (2) an average response of various patients' 110 viewing of the visual representation 108. Hence, we can transfer 806 the sequence of frames of the sample according to a predetermined pace. The resulting frames 1 808 and 2 810 are passed into the real-time visual representation processing algorithm. The algorithm enables a piecing together of a high-resolution composite that is sent to the pixel array 106. By performing this inpainting process, we can increase the patient's 110 resolution, while eliminating their need to constantly do a manual scan of the scene just to see the real world 800. That is, the overall motion experienced by the patient 110 is composed of a set of small motions to induce the super-resolution effect to address the problem of a low-number of electrodes and larger motions are needed to induce the inpainting process to address the problem of non-working electrodes.

Figure 9:
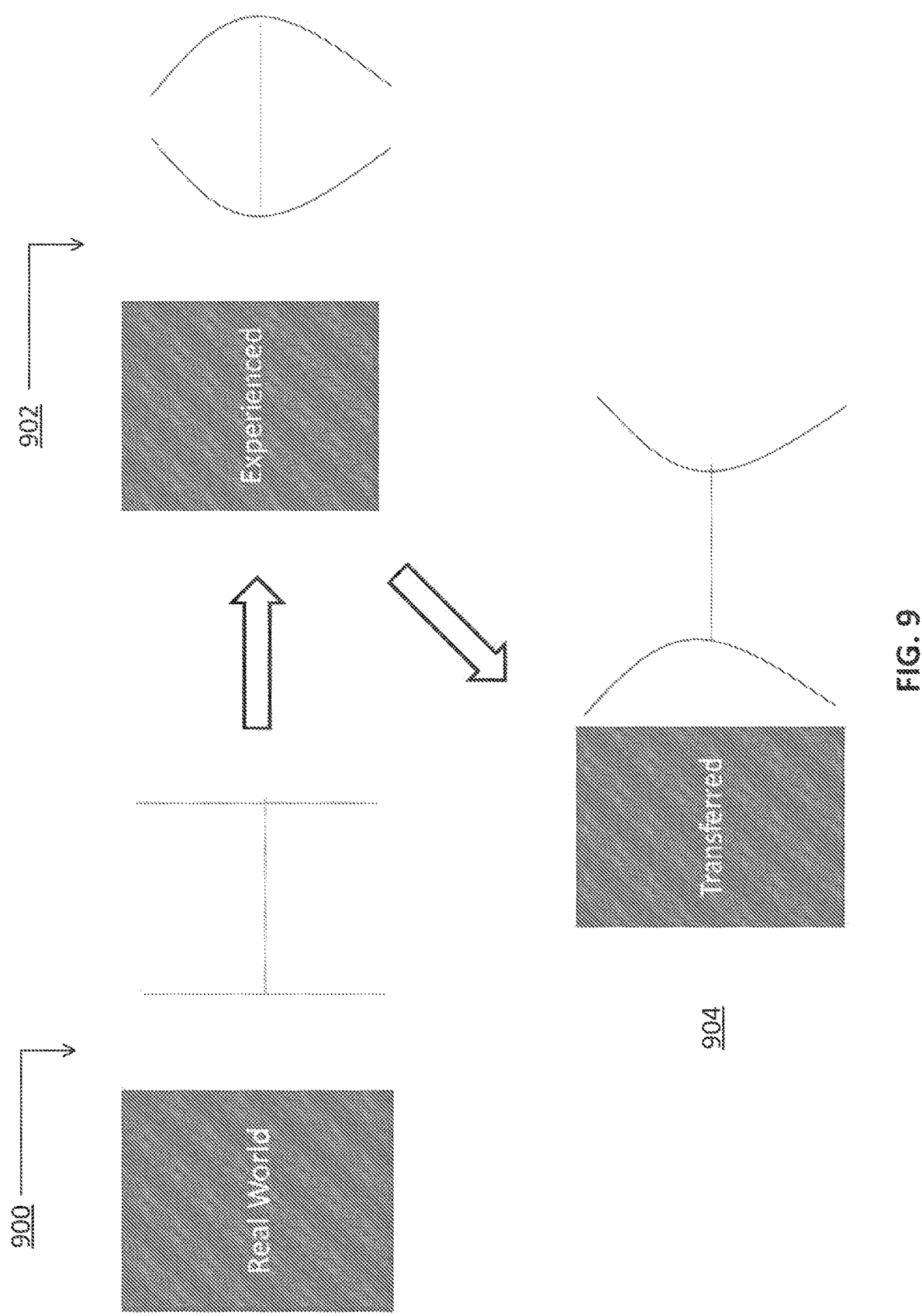
FIG. 9 is an example of a deconvolution process to enhance vision via transferring an inverse of a visual defect for systems and methods for psycho-signal processing in accordance with embodiments of the present disclosure.

FIG. 9 is an example of a deconvolution process to enhance vision via transferring an inverse of a visual defect for systems and methods for psycho-signal processing in accordance with embodiments of the present disclosure. The real world 900 shows a true state of a visual representation 108. It is what people will normal vision will see. Here, the patient 110 has a visual distortion wherein the experienced vision 902 is convoluted. That is, the patient 110 experiences 902 a convex image of the real world 900. Thus, the transferred image 904 has to be concave so that when the patient 110 receives the transferred image 904 via the pixel array 106, his vision will perform that convex bending in order for him to see the correct real world 900 image. In an example, patients 110 with phosphene vision often see convoluted versions of the real world 900. So, we can measure the patients' 110 vision and then send a convoluted version of the real world 900 to them so that when they see it, their eye will re-convolve the modified visual representation in order to get the real world 900.

Figure 10:
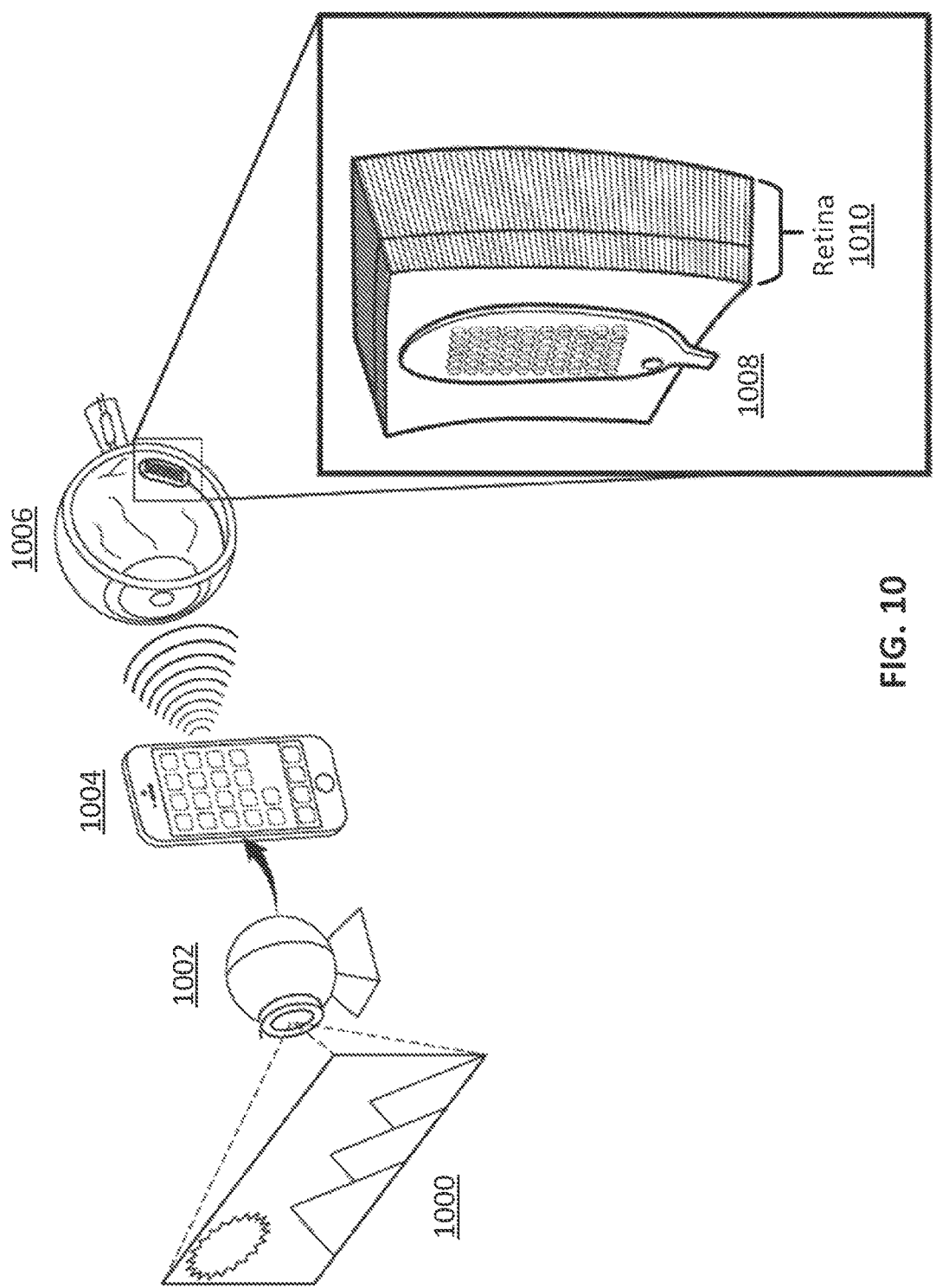
FIG. 10 is a block diagram of an example system with application for systems and methods for psycho-signal processing in accordance with embodiments of the present disclosure.

FIG. 10 is a block diagram of an example system with application for systems and methods for psycho-signal processing in accordance with embodiments of the present disclosure. Referring to FIG. 10, the system includes an image capture device 1002, a computing device 1004 that may comprise a processor and memory 104, and a pixel array 1006. In this example, the computing device 1004 may be a mobile computing device. In an example, the image capture device 1002 may be a camera, a video camera, or any other suitably similar device that can capture an image 1000. The captured image 1000 is then sent to the computing device 1004 that may comprise a processor and memory 104 for image processing via the methods described in the present disclosure. The processed image is then sent to the patient's eye 1006, specifically to the retina 1010, wherein the pixel array 1008, such as an Implanted Retinal Prostheses (IRP) as shown here, that has been implanted in the patient's eye 1006.

The above figures and present disclosure can be used to address various patient 110 conditions. For instance, when the resolution of the patient's 110 visual aid system is low. This disclosure can use the static 602 or dynamic 704 super resolution decomposition processes to enable patients 110 to see with better resolution, even if all their electrodes are working. In another example, wherein the patient 110 has non-working electrodes, we can use the inpainting process in addition to the static 602 or dynamic 704 super resolution decomposition processes as part of the real-time visual representation processing algorithm to move the scene for the patients 110, ensuring they can see the real world. In yet another example, wherein patients 110 see a convoluted distortion of the real world, we can use the real-time visual representation processing algorithm to send them a modified visual representation that they can then re-convolve to see the real world. Additionally, the present disclosure can be used to treat other conditions as well, such as macular degeneration. It could also have military applications by enhancing vision of the eye pieces worn by soldiers since the algorithm can be adapted there as well. Furthermore, the real-time visual representation processing algorithm is not computation intensive, so it can improve the computing device's 102 efficiency and speed.

The present subject matter may be a system, an apparatus, a method, and/or a computer program product. Aspects of the present subject matter are described herein with reference to flowchart illustrations and/or block diagrams of methods and apparatus/systems according to embodiments of the subject matter. It will be understood that each block of the flowchart illustrations and/or block diagrams, and combinations of blocks in the flowchart illustrations and/or block diagrams, can be implemented by computer readable program instructions.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. In another example, a computing device may be any type of conventional computer, such as a laptop computer or a tablet computer or a desktop computer. In another example, the computing device may be a type of network device such as a router or a switch. In another example, the computing device may be a smart television or a high definition television. In another example, the computing device may be a battery powered Internet of Things (IoT) device. In another example, a computing device may be a mobile computing device such as, for example, but not limited to, a smart phone, a cell phone, a pager, a personal digital assistant (PDA), a mobile computer with a smart phone client, or the like. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on servers in a datacenter, the examples may similarly be implemented on any suitable computing device or computing devices.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

The flowchart and block diagrams in the Figures illustrate the architecture, functionality, and operation of possible implementations of systems and methods according to various embodiments of the present subject matter. In this regard, each block in the flowchart or block diagrams may represent a module, segment, or portion of instructions, which comprises one or more executable instructions for implementing the present disclosure. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Thus, the order of the blocks should not be constrained therein.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A system comprising:
    an image capture device;
    a computing device comprising at least one processor and memory configured to:
        receive a visual representation of a subject;
        perform a structured motion operation on the received visual representation to generate a modified visual representation of the subject;
        use a real-time visual representation processing algorithm that comprises at least one of an image segmentation process, an image registration process, an inpainting process, a super-resolution process, and an image decomposition process to create the modified visual representation;
        determine psycho-physically relevant values for use in the real-time visual representation processing algorithm; and
    a pixel array display comprising a user interface to present the modified visual representation.

2. The system of claim 1, wherein the image segmentation process comprises detection of continuous edges of large objects within the visual representation and exclude edges of small features within the modified visual representation.

3. The system of claim 1, wherein the modified visual representation comprises a composite low-resolution video sequence of a plurality of the visual representation presented to the pixel array for the user to mentally fuse into a high-resolution visual representation.

4. The system of claim 1, wherein the at least one processor and memory is further configured to optimize at least one of an input parameter for use in the real-time visual representation processing algorithm, wherein the parameter comprises at least one of a motion smoothness parameter, a frame-rate parameter, a delay parameter between an aliased information to generate a composite low-resolution video sequence of the visual representation, and a point spread function.

5. The system of claim 1, further comprising:
    the at least one processor and memory configured to:
        determine a visual acuity measurement of a person in response to viewing the visual representation or another visual representation; and
        perform the structured motion operation comprising a planned smooth motion operation that includes panning, blurring, and down-sampling on the received visual representation based on the person's visual acuity measurement in response to viewing the modified visual representation.

6. The system of claim 1, further comprising:
    the at least one processor and memory configured to:
        determine an average response of a plurality of people to viewing the modified visual representation or another visual representation; and perform the structured motion operation comprising a planned smooth motion operation that includes panning, blurring, and down-sampling on the received visual representation based on the average response.

7. A system comprising:
an image capture device;
a computing device comprising at least one processor and memory configured to:
  measure a person's vision of a visual representation of a subject;
  generate a scan of the person's measured vision of the visual representation;
  perform a structured motion operation on the received visual representation to generate a modified visual representation of the subject for use in presenting improved visual representation of the subject;
  re-convolve the modified visual representation to generate a corrected visual representation for the person; and
a pixel array display comprising a user interface to present the modified visual representation.

8. The system of claim 7, wherein the at least one processor and memory is configured to:
  determine a visual acuity measurement of the person based on feedback from the person upon viewing the modified visual representation; and
  determine one or more aberrations in the person's eyesight based on the visual acuity measurement.

9. The system of claim 8, wherein the at least one processor and memory is configured to generate the scan of the person's measured vision of the visual representation of the subject via an optimization of the scan based on at least one of a person's visual acuity measurement to the visual representation of the subject and an average response of a plurality of people to viewing the modified visual representation.

10. The system of claim 7, wherein the modified visual representation comprises a modified convoluted visual representation generated based on the scan of the person's measured vision of the visual representation.

11. The system of claim 7, wherein the at least one processor and memory is configured to determine psychophysically relevant values for use in the real-time visual representation processing algorithm.

12. The system of claim 7, wherein the image segmentation process comprises detection of continuous edges of large objects within the modified visual representation and exclude edges of small features within the visual representation.

13. The system of claim 7, wherein the modified visual representation comprises a composite low-resolution video sequence of a plurality of the visual representation presented to the pixel array for the person to mentally fuse into a high-resolution visual representation.

14. The system of claim 13, wherein the composite low-resolution video sequence is obtained by use of a technique comprising an inverse of a Kalman Filter dynamic super-resolution algorithm.

15. The system of claim 7, wherein the at least one processor and memory is further configured to optimize at least one of an input parameter for use in a real-time visual representation processing algorithm, wherein the parameter comprises at least one of a motion smoothness parameter, a frame-rate parameter, a delay parameter between an aliased information to generate a composite low-resolution video sequence of the visual representation, and a point spread function.

16. The system of claim 7, further comprising:
the at least one processor and memory configured to:
  determine a visual acuity measurement of a person in response to viewing the modified visual representation or another visual representation; and
  perform the structured motion operation comprising a planned smooth motion operation that includes panning, blurring, and down-sampling on the received visual representation based on the person's visual acuity measurement in response to viewing the modified visual representation.

17. The system of claim 7, further comprising:
the at least one processor and memory configured to:
  determine an average response of a plurality of people to viewing the modified visual representation or another visual representation; and
  perform the structured motion operation comprising a planned smooth motion operation that includes panning, blurring, and down-sampling on the received visual representation based on the average response.

* * * * *